United States Patent [19]

Tamano et al.

[11] Patent Number: 5,681,664
[45] Date of Patent: Oct. 28, 1997

[54] HOLE-TRANSPORTING MATERIAL AND USE THEREOF

[75] Inventors: Michiko Tamano; Toshikazu Onikubo; Toshiyuki Uemura; Tadashi Ogawa; Toshio Enokida, all of Tokyo, Japan

[73] Assignee: Toyo Ink Manufacturing Co., Ltd., Tokyo, Japan

[21] Appl. No.: 510,535

[22] Filed: Aug. 2, 1995

[30] Foreign Application Priority Data

Aug. 4, 1994 [JP] Japan .................................. 6-183198
Dec. 22, 1994 [JP] Japan .................................. 6-319694

[51] Int. Cl.$^6$ .............................. B32B 7/00; H05B 33/12
[52] U.S. Cl. ...................... 428/690; 428/411.1; 428/457; 428/704; 428/917; 313/504; 313/506
[58] Field of Search ...................... 428/690, 704, 428/917, 457, 411.1; 313/504, 506

[56] References Cited

FOREIGN PATENT DOCUMENTS

| 0 052 961 | 6/1982 | European Pat. Off. . |
| 2 295 462 | 7/1976 | France . |
| 5-40350 | 2/1993 | Japan . |
| 1 535 193 | 12/1978 | United Kingdom . |

*Primary Examiner*—Marie Yamnitzky
*Attorney, Agent, or Firm*—Wenderoth, Lind & Ponack

[57] ABSTRACT

Hole-transporting materials of the following formula (1) have excellent hole-transporting capability and excellent durability,

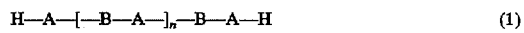

wherein A is an aromatic amine derivative residue of the following formula (2), B is a residue of the following formula (3), and n is an integer of 1 to 5,000, Formula (2):

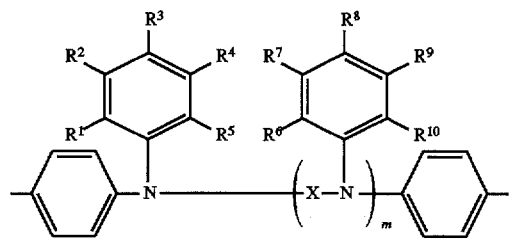

Formula (3):

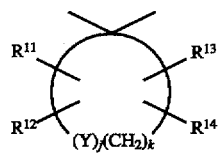

and the above hole-transporting materials therefore give an organic EL device and an electrophotographic photoreceptor which are excellent in stability in the continuous operation for a long period time.

8 Claims, 4 Drawing Sheets

HOLE-TRANSPORTING MATERIAL AND USE THEREOF

FIELD OF THE INVENTION

The present invention relates to a hole-transporting material having an aromatic amine structure, for use as a photosensitive material or an organic photoconductive material. More specifically, it relates to a hole-transporting material for use as a hole-transporting material of an organic electrolumineseence (EL) device or an electrophotographic photoreceptor.

PRIOR ART OF THE INVENTION

Organic photoconductive materials developed as photosensitive materials or hole-transporting materials are advantageous in many points, that is, they are less expensive, processable in a variety of forms and free of pollution, and many compounds have been proposed so far. As organic photoconductive materials, for example, U.S. Pat. No. 3,189,447 discloses oxadiazole derivatives; U.S. Pat. No. 3,257,203 discloses oxazole derivatives; U.S. Pat. No. 3,717,462, JP-A-54-59143 and U.S. Pat. No. 4,150,978 disclose hydrazone derivatives; U.S. Pat. No. 3,820,989, JP-A-51-93224 and JP-A-55-108667 disclose triarylpyrazoline derivatives; U.S. Pat. No. 3,180,730, U.S. Pat. No. 4,232,103, JP-A-55-144,250 and JP-A-56-119132 disclose arylamine derivatives; and JP-A-58-190953 and JP-A-59-195658 disclose stilbene derivatives.

An organic EL device is one example of using a hole-transporting material. An EL device using an organic substance is overwhelmingly expected to be usable as a solid light-emitting inexpensive large-screen full-color display device, and developments of many kinds of devices are under way. Generally, an EL device is composed of a light-emitting layer and a pair of mutually opposite electrodes sandwiching the light-emitting layer. Light emission is the following phenomenon. When an electric field is applied to these two electrodes, electrons are injected into the light-emitting layer from a cathode side and holes are injected into the light-emitting layer from an anode side. When the electrons recombine with the holes in the light-emitting layer, their energy level comes back to a valence bond band. At this time, the electrons release energy as light.

As compared with inorganic EL devices, conventional organic EL devices require high actuation voltage, and their light emission brightness and light emission efficiency are low. Further, conventional organic EL devices deteriorate in properties to a great extent, and no organic EL device has been put to practical use.

In recent years, there has been proposed an organic EL device which is produced by layering a thin film containing an organic compound having a fluorescent quantum effect so that it can emit light at a low voltage as low as less than 10 V, and it attracts attention (Appl. Phy. Lett., Vol. 51, page 913, 1987).

The above organic EL device has a fluorescent material layer formed of a metal chelate complex and a hole-injecting layer formed of an amine-containing compound, and emits green light having a high brightness. In a direct current voltage of 6 or 7V, the above organic EL device accomplishes a brightness of at least 100 cd/m² and a maximum light emission efficiency of 1.5 lm/W. That is, it achieves nearly practically usable performance.

However, conventional organic EL devices including the above organic EL device are not yet sufficient in brightness and light emission stability in their continuous operation for a long period of time. For developing an organic EL device having a higher light emission brightness, having high light emission efficiency and having excellent stability in the continuous operation for a long period time, therefore, it is desired to develop a hole-transporting material having the excellent capability of hole-transporting and high durability.

Meanwhile, an electrophotographic photoreceptor is among products for which a hole-transporting material is adapted. Electrophotography is one of the image-formation methods invented by Carlson. In this method, a photoreceptor is charged by corona discharging and then optically imagewise exposed to form an electrostatic latent image. Then, the electrostatic latent image is developed by making at toner adhere to the electrostatic latent image, and the resultant toner image is transferred to a receptor sheet. The electrophotographic photoreceptor is therefore basically required to have the following properties: to retain a proper electrical potential in a dark place, to discharge to a lower degree in a dark place, and to discharge rapidly under irradiation with light. Conventional electrophotographic photoreceptors are formed from inorganic photoconductive materials such as selenium, selenium alloy, zinc oxide, cadmium sulfide and tellurium. These inorganic photoconductive materials have advantages in that a photoreceptor formed thereof has high durability and permits printing in a large quantity. However, it is pointed out that the above inorganic photoconductive materials have defects in that they require a large production cost, have poor processability and have toxicity. For overcoming these defects, developments of photoreceptors for which organic compounds are adapted are under way, while electrophotographic photoreceptors using conventional organic photoconductive materials as a hole-transporting material are still not necessarily satisfactory in electrophotographic properties such as chargeability, sensitivity and residual potential, and it is desired to develop a hole-transporting material having excellent charge-transporting capability and excellent durability.

SUMMARY OF THE INVENTION

It is an object of the present invention to provide a hole-transporting material having excellent hole-transporting capability and excellent durability.

It is another object of the present invention to provide an organic EL device and an electrophotographic photoreceptor for which the above hole-transporting material is adapted, so that they are excellent in stability in the continuous operation for a long period time.

According to the present invention, there is provided a hole-transporting material of the formula (1),

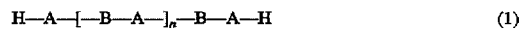

(1)

wherein A is an aromatic amine derivative residue of the following formula (2), B is a residue of the following formula (3), and n is an integer of 1 to 5,000, Formula (2):

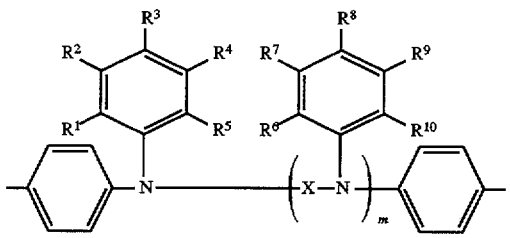

wherein each of $R^1$ to $R^{10}$ is independently hydrogen, halogen, an unsubstituted alkyl group, a substituted alkyl group, an unsubstituted alkoxy group, a substituted alkoxy group, an unsubstituted thioalkoxy group, a substituted thiolkoxy group, a cyano group, an amino group, a mono- or disubstituted amino group, a hydroxyl group, a mercapto group, an unsubstituted aryloxy group, a substituted aryloxy group, an unsubstituted arylthio group, a substituted arylthio group, an unsubstituted aromatic group, a substituted aromatic group, an unsubstituted heterocyclic group or a substituted heterocyclic group, provided that adjacent substituents among $R^1$ to $R^{10}$ may form substituted or unsubstituted ring or rings, X is a divalent aromatic residue or —Ar—Z—Ar— in which each Ar is an aromatic residue having 6 to 20 carbon atoms and Z is a direct bond, oxygen, sulfur, selenium, an aromatic residue which may contain any one of oxygen, sulfur and selenium, or a divalent aliphatic residue which may contain any one of oxygen, sulfur and selenium, and m is an integer of 0 or 1, Formula (3):

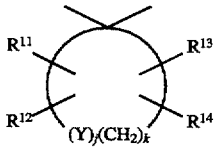

wherein each of $R^{11}$ to $R^{14}$ is independently hydrogen, halogen, an unsubstituted alkyl group, a substituted alkyl group, an unsubstituted alkoxy group, a substituted alkoxy group or a disubstituted amino group, provided that adjacent substituents among $R^{11}$ to $R^{14}$ may form a substituted or unsubstituted ring, Y is oxygen, sulfur or monosubstituted nitrogen, j is an integer of 0 or 1, k is an integer of 4 to 7.

Further, according to the present invention, there is provided an organic EL device having a pair of electrodes and a light-emitting layer formed of at least one layer of an organic compound placed between the electrodes, in which at least one layer of the layers the forming the light-emitting layer contains the above hole-transporting material.

Further, according to the present invention, there is provided an electrophotographic photoreceptor produced by coating a charge-generating material and a hole-transporting material on an electrically conductive material, in which the hole-transporting material is the above hole-transporting material.

DETAILED DESCRIPTION OF THE INVENTION

Figure 1:
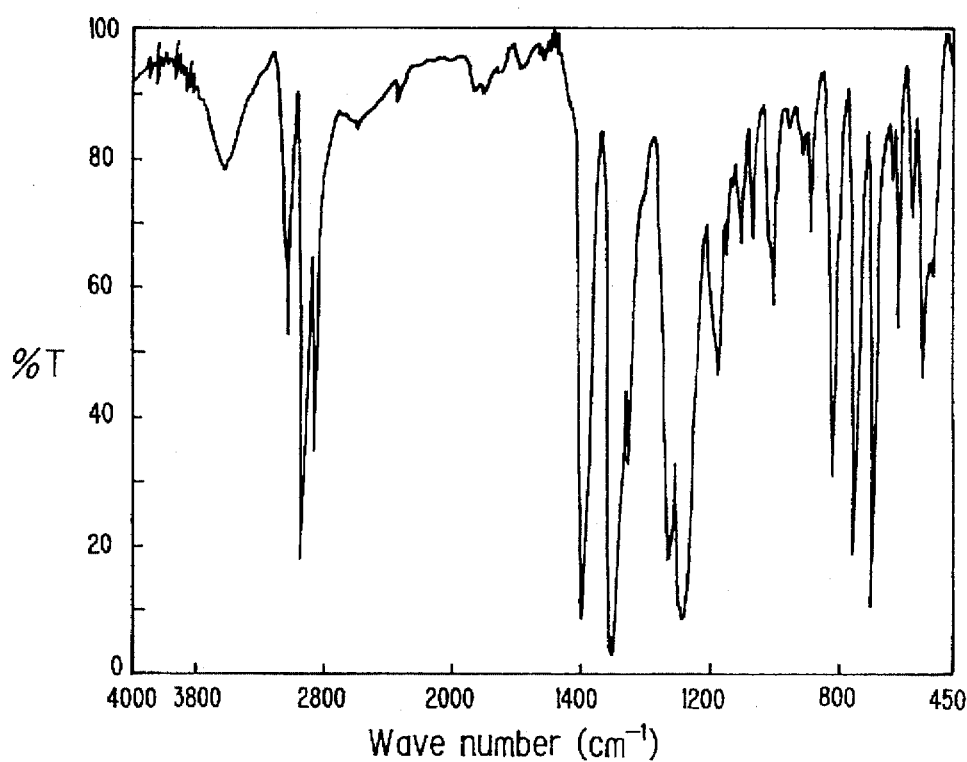
FIG. 1 shows the infrared absorption spectrum of Compound 1.

The hole-transporting material provided by the present invention has the following formula (1), $$H-A-[-B-A-]_n-B-A-H \qquad (1)$$

wherein A is an aromatic amine derivative residue of the above formula (2), B is a residue of the above formula (3), and n is an integer of 1 to 5,000.

In the formula (2), each of $R^1$ to $R^{10}$ is independently hydrogen, halogen, an unsubstituted alkyl group, a substituted alkyl group, an unsubstituted alkoxy group, a substituted alkoxy group, an unsubstituted thioalkoxy group, a substituted thioalkoxy group a cyano group, an amino group, a mono- or disubstituted amino group, a hydroxyl group, a mercapto group, an unsubstituted aryloxy group, a substituted aryloxy group, an unsubstituted arylthio group, a substituted arylthio group, an unsubstituted aromatic group, a substituted aromatic group, an unsubstituted heterocyclic group or a substituted heterocyclic group, provided that adjacent substituents among $R^1$ to $R^{10}$ may form substituted or unsubstituted ring or rings.

The halogen includes fluorine, chlorine, bromine and iodine. The unsubstituted alkyl group includes methyl, ethyl, propyl, butyl, see-butyl, tert-butyl, pentyl, hexyl, heptyl, octyl and stearyl. The substituted alkyl group includes trichloromethyl, trifluoromethyl, cyclopropyl, cyclohexyl, 1,3-cyclohexadienyl, 2-cyclopenten-1-yl, 2,4-cyclopentadien-1-ylidenyl. The unsubstituted alkoxy group includes methoxy, ethoxy, propoxy, n-butoxy, sec-butoxy, tert-butoxy, pentyloxy, hexyloxy and stearyloxy. The substituted alkoxy group includes trifluoromethoxy and 1,1,2,2-tetrafluoroethoxy. The unsubstituted thioalkoxy group includes methylthio, ethylthio, propylthio, butylthio, sec-butylthio, tert-butylthio, pentylthio, hexylthio, heptylthio and octylthio. The substituted thioalkoxy group includes 1,1,1-trifluoromethyl and 1,1,2,2-tetrafluoroethylthio.

The mono- or disubstituted amino group includes methylamino, dimethylamino, ethylamino, diethylamino, dipropylamino, dibutylamino, diphenylamino, bis(acetoxymetyl)amino, bis(acetoxyethyl)amino, bis(acetoxypropyl)amino, bis(acetoxybutyl)amino and dibenzylamino. The unsubstituted aryloxy group includes phenoxy and p-tert-butylphenoxy. The substituted aryloxy group includes 3-fluorophenoxy and 4-(1,1,1-trifluoromethyl)phenoxy. The unsubstituted arylthio group includes phenylthio. The substituted arylthio group includes 3-fluorophenylthio. The substituted and unsubstituted aromatic groups include phenyl, biphenylenyl, triphenylenyl, tetraphenylenyl, 3-nitrophenyl, 4-methylthiophenyl, 3,5-dicyanophenyl, o-, m- and p-tolyl, xylyl, o-, m- and p-cumenyl, mesityl, pentalenyl, indenyl, naphthyl, azulenyl, heptanlenyl, acenaphthylenyl, phenalenyl, fluorenyl, anthryl, anthraquinonyl, 3-methylanthryl, phenanthryl, triphenylenyl, pyrenyl, chrysenyl, 2-ethyl-1-crysenyl, picenyl, perylenyl, 6-chloroperylenyl, pentaphenyl, pentacenyl, tetraphenylenyl, hexaphenyl, hexacenyl, rubicenyl, coronenyl, trinaphthylenyl, heptaphenyl, pyranthrenyl and ovalenyl.

The substituted and unsubstituted heterocyclic groups include thionyl, furyl, pyrrolyl, imidazolyl, pyrazolyl, pyridyl, pyrazinyl, pyrimidinyl, pyridazinyl, indolyl, quinolyl, isoquinolyl, phthalazinyl, quinoxalinyl, quinazolinyl, carbazolyl, acridinyl, phenadinyl, furfuryl, isothiazolyl, isoxazolyl, furazanyl, phenoxaziyl, benzothiazolyl, benzoxazolyl, benzimidazolyl, 2-methylpyridyl and 3-cyanopyridyl, although the heterocyclic groups shall not be limited to these.

Further, adjacent substituents as $R^1$ to $R^{10}$ may form a 5- to 7-membered aliphatic, aromatic or heterocyclic ring which may contain an oxygen, nitrogen or sulfur atom. Further, this aliphatic, aromatic or heterocyclic ring may further have a substituent in any position.

As $R^1$ to $R^{10}$, preferred are hydrogen, an unsubstituted alkyl group, an unsubstituted alkoxy group and a dialkyl-substituted amino group.

In the formula (2), X is a divalent aromatic residue or —Ar—Z—Ar— in which each Ar is an aromatic residue having 6 to 20 carbon atoms and Z is a direct bond, oxygen, sulfur, selenium, an aromatic residue which may contain any one of oxygen, sulfur and selenium, or a divalent aliphatic residue which may contain any one of oxygen, sulfur and selenium.

The above divalent aromatic residue includes 1,4-phenylene, 1,3-phenylene, 1,2-phenylene, 4,4'-biphenylene, 4,4'-(3,3'-dimethyl)biphenylene, 4,3'(2,2'-dimethyl)biphenylene, 3,3'(2,2'-dichloro)biphenylene, 4,4'(3,3',5,5'-tetramethyl)biphenylene, 4,4'(3,3'-dimethoxy)biphenylene, p,p-terphenylene, p,m-terphenylene, 1,8-naphthylene, 1,5-naphthylene, 1,4-naphthylene, 2,7-naphthylene, 9,10-anthranylene, 1,8-anthranylene, 1,5-anthranylene, 1,4-anthranylene, 2,6-anthranylene, 9,10-phenanthrelene, 1,8-phenanthrelene, 9,9-fluorenylene, 2,7-fluoronylene, 1,3-pyrenylene, 3,8-pyrenylene and 9,9'-biphenyl-fluorenylene groups.

Ar in the —Ar—Z—Ar— is an aromatic residue having 6 to 20 carbon atoms such as 1,4-phenylene, 1,3-phenylene, 1,2-phenylene, 4,4'-biphenylene, 4,4'(3,3'-dimethyl) biphenylene, 4,3'(2,2'-dimethyl)biphenylene, 3,3'(2,2'-dichloro)biphenylene, 4,4'(3,3,5,5-tetramethyl)biphenylene, 4,4'(3,3'-dimethoxy)biphenylene, p,p-terphenylene, p,m-terphenylene, 1,8-naphthylene, 1,5-naphthylene, 1,4-naphthylene, 2,7-naphthylene, 9,10-anthranylene, 1,8-anthranylene, 1,5-anthranylene, 1,4-anthranylene, 2,6-anthranylene, 9,10-phenanthrelene, 1,8-phenanthrelene, 9,9-fluorenylene, 2,7-fluoronylene, 1,3-pyrenylene, 3,8-pyrenylene and 9,9'-biphenyl-fluorenylene groups.

Z in the —Ar—Z—Ar— is a direct bond, oxygen, sulfur, selenium, an aromatic residue which may contain any one of oxygen, sulfur and selenium, or a divalent aliphatic residue which may contain any one of oxygen, sulfur and selenium. The above divalent aromatic residue includes 2,5-furanylene, 2,5-thiophenylene, 4,4-N-methylpyrelizylenylene, 4,4-chromanylene, 1,1-(1,2,3-trihydro)indenylene, 1,1-(1,2,3,4-tetrahydro)naphthalenin, 2,2-(1,2,3,4-tetrahydro)naphthalenin and stilbenylene groups. The above divalent aliphatic residue includes 1,1-(4-methyl)cyclohexynylene, 1,1-furanylenyl, 1,1-thiophenylenyl, 1,1-(1,2,3-trihydro)indenylene, 1,1-(1,2,3,4-tetrahydronaphthalenin, 2,2-(1,2,3,4-tetrahydro) naphthalenin, and bis(trifluoromethyl)methylene groups.

As X, preferred are phenylene, biphenylene, substituted biphenylene, terphenylene, naphthylene and anthranylene groups.

In the formula (2), m is an integer of 0 or 1.

Table 1 shows typical examples of the substituted or unsubstituted aromatic amine derivative residue of the formula (2), while the residue of the formula (2) shall not be limited to these.

TABLE 1

| (A) | Chemical Structure |
|---|---|
| (1) | 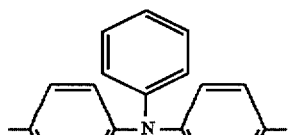 |
| (2) | 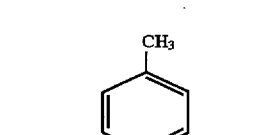 |

TABLE 1-continued

| (A) | Chemical Structure |
|---|---|
| (3) | triphenylamine with n-C$_4$H$_9$ substituent |
| (4) | triphenylamine with n-C$_8$H$_{17}$ substituent |
| (5) | triphenylamine with n-C$_4$H$_9$ and CH$_3$ substituents |
| (6) | triphenylamine with m-OCH$_3$ substituent |
| (7) | triphenylamine with p-OCH$_3$ substituent |
| (8) | triphenylamine with 3,5-di-CH$_3$ substituents |
| (9) | triphenylamine with p-N(CH$_3$)$_2$ substituent |

TABLE 1-continued
| (A) | Chemical Structure |
|---|---|
| (10) | 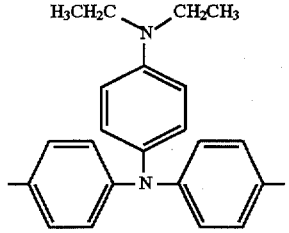 |
| (11) | 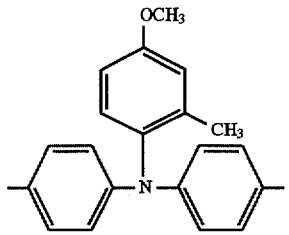 |
| (12) | 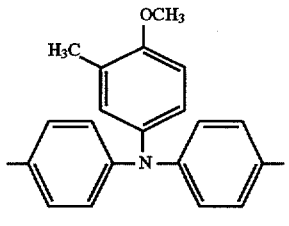 |
| (13) | 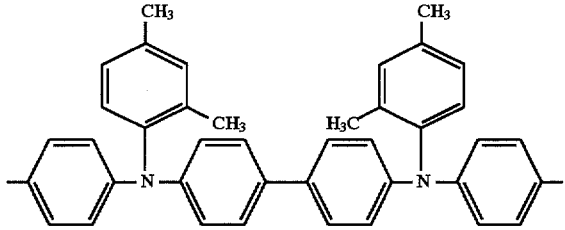 |
| (14) | 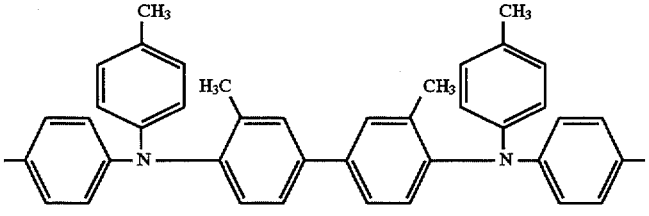 |
| (15) | 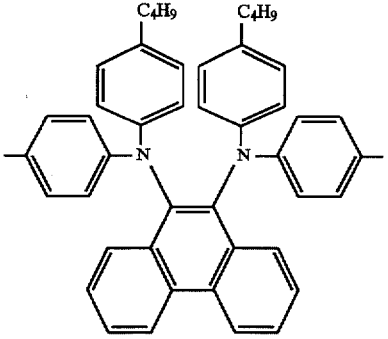 |

TABLE 1-continued

| (A) | Chemical Structure |
|---|---|
| (16) | 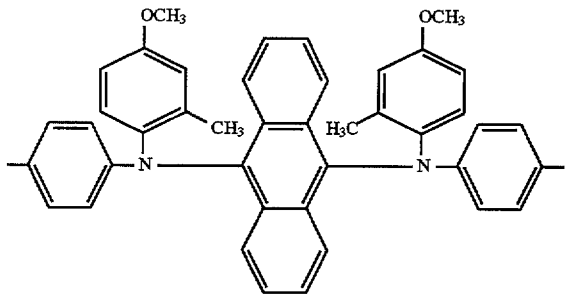 |
| (17) | 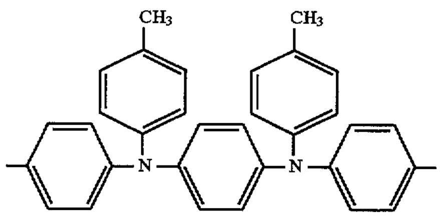 |
| (18) | 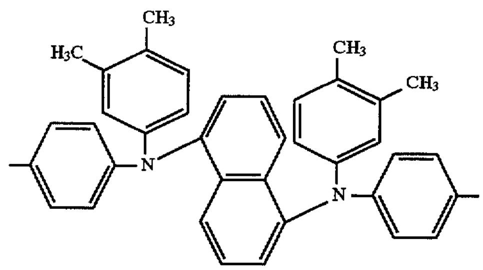 |
| (19) | 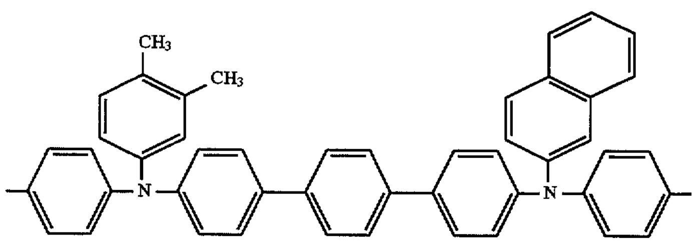 |
| (20) | 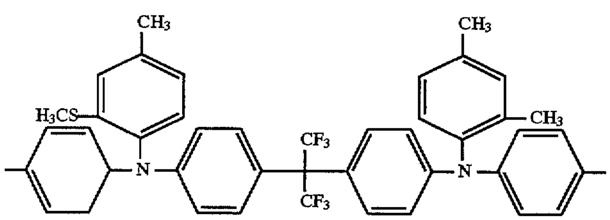 |
| (21) | 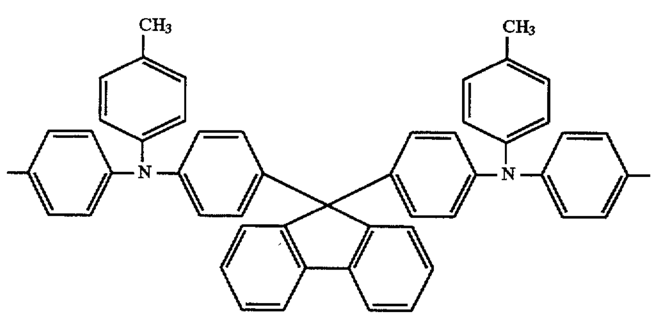 |

TABLE 1-continued
| (A) | Chemical Structure |
|---|---|
| (22) | 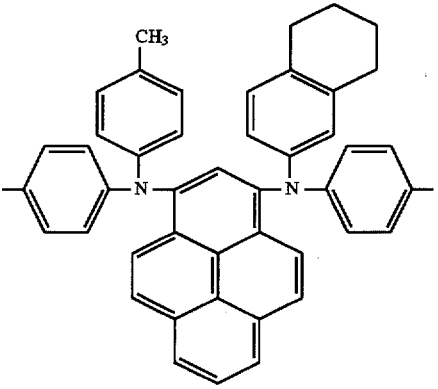 |
| (23) | 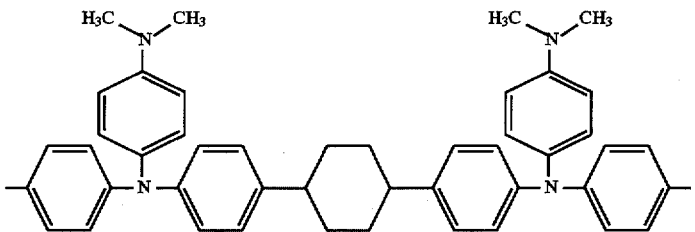 |
| (24) | 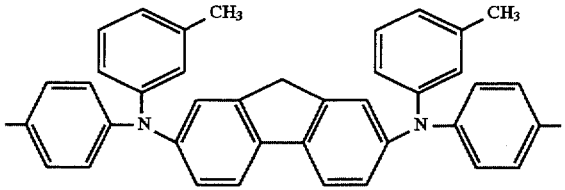 |
| (25) | 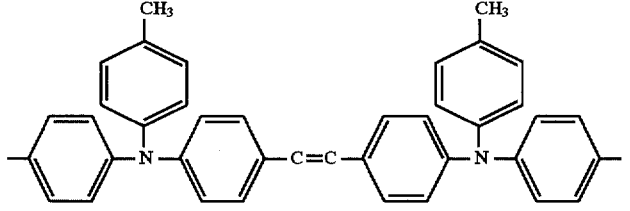 |
| (26) | 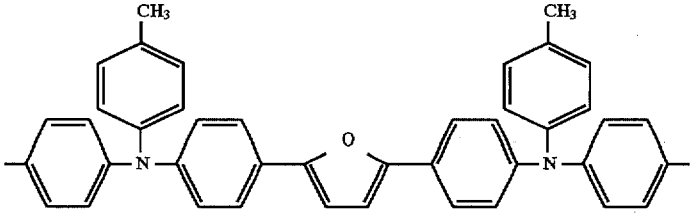 |
| (27) | 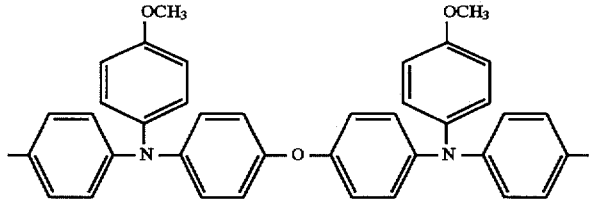 |

TABLE 1-continued
| (A) | Chemical Structure |
|---|---|
| (28) | 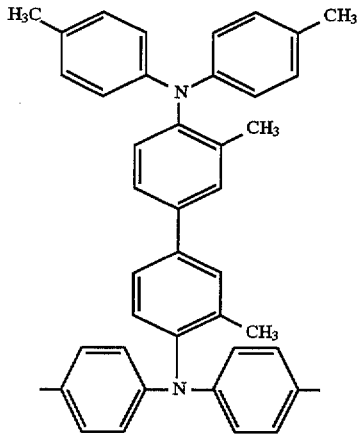 |
| (29) | 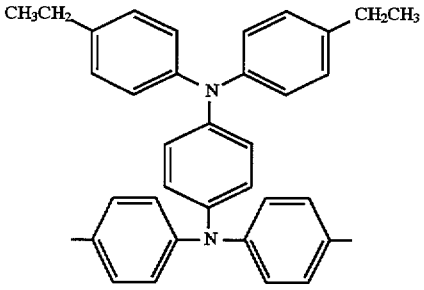 |
| (30) | 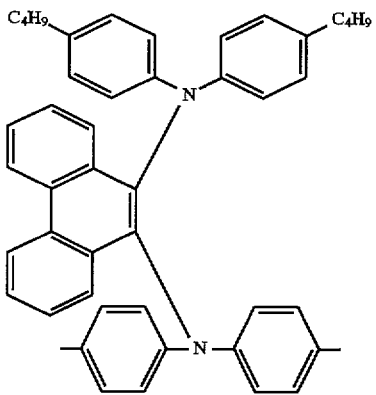 |
| (31) | 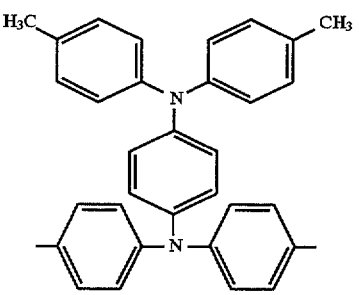 |

TABLE 1-continued

| (A) | Chemical Structure |
|---|---|
| (32) | 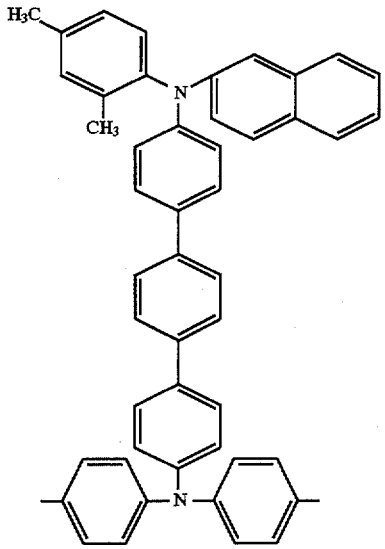 |
| (33) | 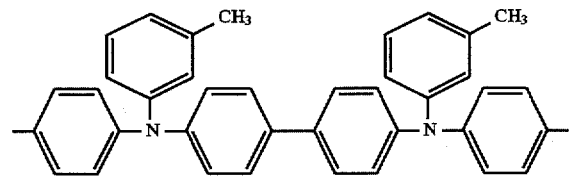 |
| (34) | 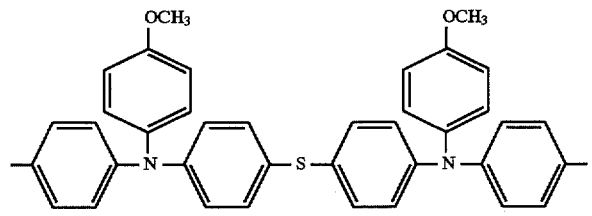 |
| (35) | 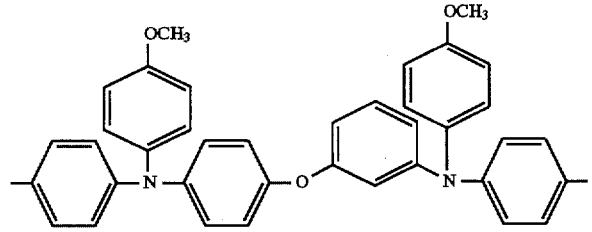 |

In the formula (3), each of $R^{11}$ to $R^{14}$ is independently hydrogen, halogen, an unsubstituted alkyl group, a substituted alkyl group, an unsubstituted alkoxy group, a substituted alkoxy group or a disubstituted amino group, provided that adjacent subsituents among $R^{11}$ to $R^{14}$ may form a substituted or unsubstituted ring.

Typical examples of $R^{11}$ to $R^{14}$ include those described concerning the compound of the formula (2) in which $R^1$ to $R^{10}$ are hydrogen, halogen, an unsubstituted alkyl group, a substituted alkyl group, an unsubstituted alkoxy group, a substituted alkoxy group or a disubstituted amino group.

In the formula (3), Y is oxygen, sulfur or monosubstituted nitrogen, j is an integer of 0 or 1 and k is an integer of 4 to 7.

Examples of the compound of the formula (3) preferably include 1,1-cyclopentylene, 1,1-cyclohexylene, 1,1-(4-methyl)cyclohexylene, 1,1-(3-methyl)cyclohexylene, 1,1-(2-methyl)cyclohexylene, 1,1-(2,6-dimethyl)cyclohexylene, 1,1-(3,3,5-trimethyl)cyclohexylene, 1,1-(3,4,4,5-trimethyl) cyclohexylene, 1,1-cycloheptylene, 1,1-cyclooctylene, N-methyl-1,1-pyrelizylenylene, 1,1-furanylenylene, 1,1-thiophenylene, 1,1-(1,2,3-trihydro)indenylene, 1,1-(1,2,3,4-tetrahydro)naphthalenin, and 2,2-(1,2,3,4-tetrahydro) naphthalenin groups. Table 2 shows specific examples of the compound of the formula (3). As the compound of the formula (3), preferred are 1,1-cyclopentylene, 1,1-cyclohexylene, 1,1-cycloheptylene and 1,1-cyclooctylene groups and any one of these in which alkyl is substituted.

TABLE 2

| (B) | Chemical Structure |
|---|---|
| (1) | 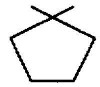 |
| (2) | 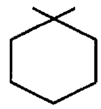 |
| (3) | 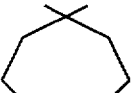 |
| (4) | 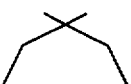 |
| (5) | 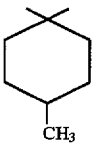 |
| (6) | 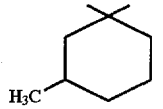 |
| (7) | 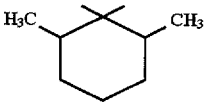 |
| (8) | 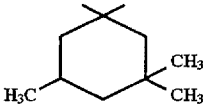 |
| (9) | 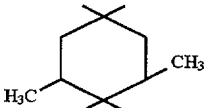 |
| (10) | 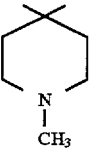 |
| (11) | 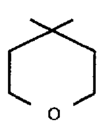 |
| (12) | 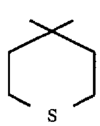 |

TABLE 2-continued

| (B) | Chemical Structure |
|---|---|
| (13) | 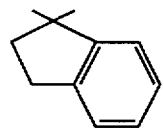 |
| (14) | 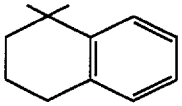 |
| (15) | 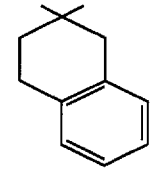 |

The compound of the formula (1), provided by the present invention, can be synthesized, for example, by the following method.

That is, an alleycite carbonyl compound such as substituted or unsubstituted aldehyde, ketone or the like and 0.5 to 4 mol, per mole of the alicyclic carbonyl compound, of an aromatic amine compound are dehydratively reacted in acetic acid as a solvent in the co-presence of methanesulfonic acid as an acid catalyst at 100° C. for 30 hours, whereby the compound of the formula (1) is obtained. In the present invention, the methanesulfonic acid as a catalyst may be replaced with an organic acid such as trifluoroacetic acid or p-toluenesulfonic acid, sulfuric acid, hydrochloric acid or a Lewis acid. The acetic acid as a solvent may be replaced with 1,4-dioxane, ether or petroleum ether.

Table 3 shows typical examples of the compound of the formula (1), while the compound of the formula (1) shall not be limited to these.

TABLE 3

| Compound | A | B | n *a) |
|---|---|---|---|
| (1) | 1 | 2 | 1 |
| (2) | 2 | 2 | 4 |
| (3) | 3 | 2 | 11 |
| (4) | 3 | 2 | 31 |
| (5) | 4 | 2 | 16 |
| (6) | 4 | 2 | 32 |
| (7) | 1 | 2 | 90 |
| (8) | 2 | 2 | 33 |
| (9) | 5 | 2 | 123 |
| (10) | 2 | 2 | 587 |
| (11) | 5 | 2 | 43 |
| (12) | 8 | 2 | 15 |
| (13) | 7 | 2 | 9 |
| (14) | 7 | 2 | 20 |
| (15) | 6 | 2 | 6 |
| (16) | 9 | 2 | 41 |
| (17) | 10 | 2 | 387 |
| (18) | 11 | 2 | 48 |
| (19) | 12 | 2 | 6 |
| (20) | 12 | 2 | 16 |
| (21) | 17 | 2 | 7 |
| (22) | 13 | 5 | 2 |
| (23) | 14 | 1 | 11 |
| (24) | 17 | 5 | 6 |
| (25) | 15 | 1 | 16 |
| (26) | 16 | 6 | 14 |

TABLE 3-continued

| Compound | A | B | n *a) |
|---|---|---|---|
| (27) | 16 | 3 | 53 |
| (28) | 17 | 1 | 18 |
| (29) | 17 | 4 | 23 |
| (30) | 18 | 5 | 525 |
| (31) | 19 | 9 | 43 |
| (32) | 19 | 8 | 15 |
| (33) | 20 | 11 | 38 |
| (34) | 20 | 10 | 100 |
| (35) | 21 | 2 | 450 |
| (36) | 20 | 9 | 34 |
| (37) | 35 | 10 | 115 |
| (38) | 21 | 12 | 230 |
| (39) | 34 | 15 | 43 |
| (40) | 22 | 13 | 19 |
| (41) | 23 | 14 | 50 |
| (42) | 24 | 7 | 10 |
| (43) | 25 | 6 | 11 |
| (44) | 33 | 5 | 1 |
| (45) | 27 | 12 | 48 |
| (46) | 28 | 8 | 16 |
| (47) | 29 | 11 | 38 |
| (48) | 30 | 9 | 6 |
| (49) | 31 | 3 | 26 |
| (50) | 32 | 6 | 18 |

*a) n obtained based on average molecular weight

The hole-transporting material of the present invention may be used as a mixture with other hole- or electron-transporting material in one layer. The hole-transporting material of the present invention is very effective since it is excellent in hole-transporting capability.

An organic EL device has at least one organic thin film between an anode and a cathode. When the organic EL device has one organic thin film (single-layer type), the organic thin film is a light-emitting layer. The light-emitting layer contains a light-emitting material, and in addition to the light-emitting material, it may contain a hole-transporting material for transporting holes to be injected from the anode to the light-emitting material or an electron-transporting material for transporting electrons to be injected from the cathode to the light-emitting material. The light-emitting material contains a hole-transporting material or an electron-transporting material in some cases. The organic EL device of a multi-layer type has a structure of anode/hole-injecting layer/light-emitting layer/cathode, anode/light-emitting layer/electron-injecting layer/cathode, or anode/hole-injecting layer/light-emitting layer/electron-injecting layer/cathode. The compound of the formula (1) can be used for an organic EL device having any one of the above layer structures. The compound of the formula (1) has high hole-transporting capability so that it can be used as a hole-transporting material in any one of the hole-injecting layer and the light-emitting layer.

Figure 5:
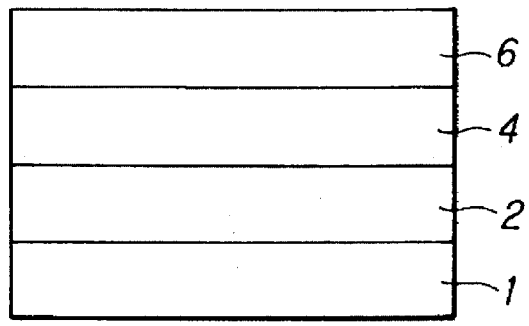
FIG. 5 is a schematic cross-sectional view of an organic EL device used in Examples.
Figure 6:
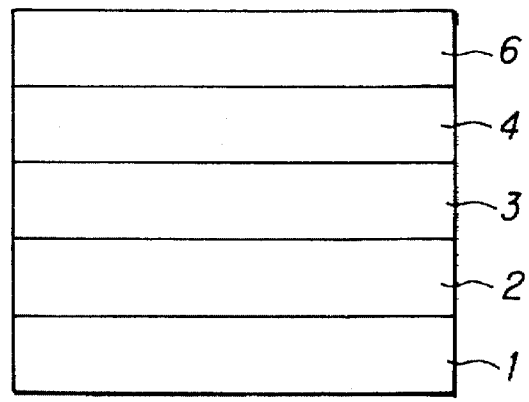
FIG. 6 is a schematic cross-sectional view of an organic EL device used in Examples.
Figure 7:
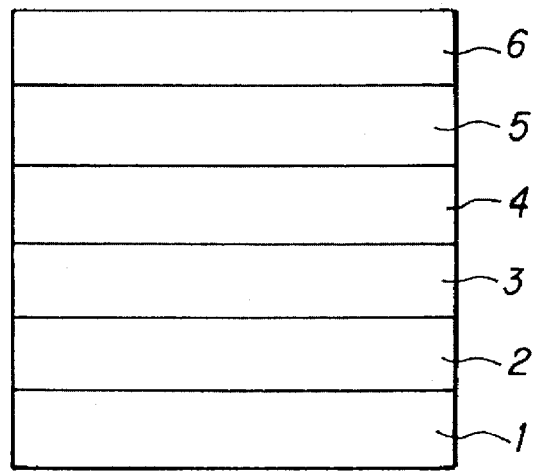
FIG. 7 is a schematic cross-sectional view of an organic EL device used in Examples.

FIGS. 5 to 7 show schematic structures of organic EL devices having the above structures. In FIGS. 5 to 7, numeral 1 indicates a substrate, numeral 2 indicates an electrode A, and numeral 6 indicates an electrode B. The electrode A is an anode, and the electrode B is a cathode. FIG. 5 shows an organic EL device of a single layer type, in which a light-emitting layer 4 is provided between the cathode and the anode. FIG. 6 shows an organic EL device of a two-layer type, in which a hole-injecting layer 3 and a light-emitting layer 4 are provided between the cathode and the anode. FIG. 7 shows an organic EL device of a three-layer type, in which a hole-injecting layer 3, a light-emitting layer 4 and an electron-injecting layer 5 are provided between the cathode and the anode.

In addition to the compound of the formula (1), the light-emitting layer may contain a light-emitting material, a doping material, a hole-transporting material for carrier transportation, and an electron-transporting material as required. The organic EL device of a two-layer type has a structure in which the light-emitting layer and the hole-injecting layer are separately provided. In this structure, the efficiency of hole-injecting from the hole-injecting layer to the light-emitting layer improves, and the light emission brightness and the light emission efficiency can be increased. In this structure, preferably, the light-emitting layer is formed from a light-emitting substance which itself has electron-transporting capability, or the light-emitting layer contains an electron-transporting material. The organic EL device of a two-layer type has another structure in which a light-emitting layer and an electron-injecting layer are provided. In this structure, preferably, the light-emitting material itself has the capability of hole-transporting, or the light-emitting layer contains a hole-transporting material.

The organic EL device of three-layer type has a light-emitting layer, a hole-injecting layer and an electron-injecting layer, so that the efficiency of re-combination of holes and electrons in the light-emitting layer is improved. The so-formed multi-layer structure can prevent a quenching-induced decrease in the brightness or life of the device. For the organic EL device of a multi-layer structure, there may be used a light-emitting material, a doping material, a hole-transporting material for earlier transportation, and an electron-transporting material in combination as required. Further, each of the hole-injecting layer, the light-emitting layer and the electron-injecting layer may be formed of at least two layers.

The electrically conductive material used for the anode of the organic EL device is preferably selected from those having a work function of greater than 4 eV. This electrically conductive material includes carbon, aluminum, vanadium, iron, cobalt, nickel, tungsten, silver, gold, platinum, palladium, alloys of these, metal oxides such as tin oxide and indium oxide called ITO substrate or NESA substrate, and organic electrically conductive resins such as polythiophene and polypyrrole.

The electrically conductive material used for the cathode is preferably selected from those having a work function of smaller than 4 eV. This electrically conductive material includes magnesium, calcium, tin, lead, titanium, yttrium, lithium, ruthenium, manganese and alloys of these, while it shall not be limited to these. Each of the anode and the cathode may be formed of at least two layers.

For the effective light emission of the organic EL device, at least one of the electrodes is desirably transparent in the light emission wavelength region of the device. Further, the substrate is desirably transparent. The transparent electrode is produced from the above electrically conductive material by a deposition method or a sputtering method such that a predetermined transparency is secured. The electrode which forms a light emission surface preferably has a light transmittance of at least 10%.

The substrate is not specially limited if it has mechanical and thermal strength and is transparent. For example, it is selected from transparent resin substrates such as a glass substrate, a polyethylene substrate, a polyether sulfone substrate and a polypropylene substrate.

Each of the layers forming the organic EL device of the present invention can be formed by any one of dry film forming methods such as a vacuum deposition method and sputtering method and wet film forming methods such as spin coating method and a dipping method. The thickness of each layer is not specially limited, while each layer is required to have a proper thickness. When the layer thickness is too large, a high voltage is required to achieve predetermined emission of light, which is poor in efficiency. When the layer thickness is too small, the layer is liable to have a pinhole, etc., so that sufficient light emission brightness is hard to obtain when an electric field is applied. Generally, the thickness of each layer is preferably in the range of from 5 nm to 10 μm, more preferably 10 nm to 0.2 μm.

In the wet film forming method, a material for forming each layer is dissolved or dispersed in a proper solvent, and a thin film is formed from the solution or dispersion. The solvent is selected from chloroform, tetrahydrofuran and dioxane, while the solvent shall not be limited to these. For improving the film formability and preventing the occurrence of pinholes, or for other purpose, the above solution or dispersion for forming each layer may contain a proper resin and/or a proper additive.

In the present invention, the above resin includes insulating resins such as polystyrene, polycarbonate, polyarylate, polyester, polyamide, polyurethane, polysulfone, polymethyl methacrylate and cellulose, photoconductive resins such as poly-N-vinylcarbozole and polysilane, and electrically conductive resins such as polythiophene and polypyrrole. The above additive includes an antioxidant, an ultraviolet absorbent and a plasticizer.

Although not specially limited, the light-emitting material or the doping material used for the organic EL device of the present invention includes anthracene, naphthalene, phenanthrene, pyrerio, tetracone, coronene, chrysene, fluorecein, perylene, phthaloperylene, naphthaloperylene, perinone, phthaloperinone, naphthaloperinone, diphenylbutadiene, tetraphenylbutadiene, coumarin, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyrane, thiopyrane, polymethine, merocyanine, an imidazole-chelated oxynoid compound, quinacridone, rubreno, and derivatives of these.

The hole-transporting material that can be used in combination with the hole-transporting material of the formula (1) is selected from compounds which have hole-transporting capability, have an excellent effect of injecting holes into the light-emitting layer or a light-emitting material, prevent the movement of excitons generated in the light-emitting into the electron-injecting layer or the electron-transporting material and have excellent thin-film formability. Specifically, the above hole-transporting material includes a phthalocyanine compound, a naphthalocyanine compound, a porphyrin compound, oxadiazole, triazole, imidazole, imidazolone, imidazolthione, pyrazoline, pyrazolone, tetrabydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and a electrically conductive polymer, although the above hole-transporting material shall not be limited to these.

The electron-injecting material is selected from compounds which have electron-transporting capability, have an excellent effect of injecting electrons into the light-emitting layer or a light-emitting material, prevent the movement of excitons generated in the light-emitting into the hole-injecting layer or the hole-transporting material and have excellent thin-film formability. The electron-injecting material includes fluorenone, anthraquinodimethane, diphenoquinone, thiopyran dioxide, oxadiazole, perylenetetracarboxylic acid, fluorenylidenemethane, anthraquinodimethane, anthrone, and derivatives of these, although the electron-transporting material shall not be limited to these. The sensitivity of the hole-transporting material can be increased by incorporating an electron-accepting substance, and the sensitivity of the electron-transporting material can be increased by incorporating an electron-donating substance.

The compound of the formula (1), provided by the present invention, can be used as a material for any layer of the organic EL device, and the compound of the formula (1) may be contained in one layer in combination with at least one of a light-emitting material, a doping material, a hole-transporting material and an electron-transporting material.

For improving the organic EL device of the present invention in the stability against temperature, humidity and ambient atmosphere, a protective layer may be formed on the surface of the device, or the device as a whole may be sealed with a silicon oil, etc.

When the compound of the formula (1) is used as a raw material for forming layer(s) constituting the organic EL device, the light emission efficiency and brightness can be increased. Further, the so-produced organic EL device is remarkably stable against heat and electric current and gives practically usable light emission brightness at a lower voltage, so that the deterioration of the device, a vital problem of prior art devices, can be remarkably decreased.

The organic EL device of the present invention can be applied to a flat panel display of a wall-mountable TV set, a plane light-emitter, a light source for a copying machine or a printer, a light source for a liquid crystal display or a counter, a display board and a sign lamp. The organic EL device of the present invention is therefore greatly industrially valuable.

The application of the compound of the formula (1) to an electrophotographic photoreceptor will be explained hereinafter. The compound of the formula (1) may be used in any layer of the electrophotographic photoreceptor, while it is desirably used as a hole-transporting material since it has high hole-transporting capability. The compound of the formula (1) functions as a hole-transporting material and gives a fast-response photoreceptor which can very effectively transport electric charge generated by optical absorption. Further, the compound of the formula (1) is excellent in ozone resistance and optical stability and therefore gives a photoreceptor excellent in durability.

The electrophotographic photoreceptor includes a photoreceptor of a single-layer type obtained by forming a photoconductive layer of a charge-generating material or a photoreceptor of a dispersion of a charge-generating material in a binder resin on an electrically conductive substrate, and a photoreceptor of a multi-layer type obtained by forming on an electrically conductive substrate, an undercoat layer, a charge-generating layer and a hole-transporting layer in this order or by forming on an electrically conductive substrate or on an undercoat layer, a hole-transporting layer and a charge-generating layer in this order. The above undercoat layer is optional. The above photoreceptor may be provided with an overcoat layer for protecting its surface from active gas and preventing filming.

Figure 8:
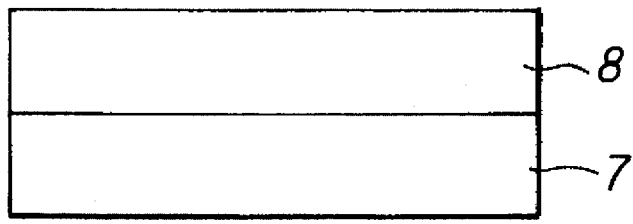
FIG. 8 is a schematic cross-sectional view of an electrophotographic photoreceptor used in Examples.
Figure 9:
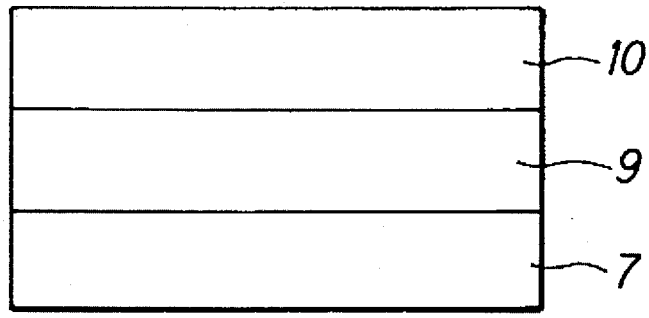
FIG. 9 is a schematic cross-sectional view of an electrophotographic photoreceptor used in Examples.

FIGS. 8 and 9 are schematic cross-sectional views of electrophotographic photoreceptors explained above. FIG. 8 shows the cross-sectional view of a photoreceptor of a single-layer type having an electrically conductive substrate 7 such as an aluminum substrate and a photoconductive layer 8 formed thereon. FIG. 9 shows the cross-sectional view of a photoreceptor of a multi-layer type having an electrically conductive on which a charge-generating layer 9 and a hole-transporting layer 10 are consecutively formed.

The charge-generating material includes organic compounds such as bisazo, guinacridone, diketopyrrolopyrrole, indigo, perylene, perinone, polycyclic quinone, squalirium salt, azulenium salt, phthalocyanine and naphthalocyanine and inorganic materials such as selenium, selenium-tellurium alloy, cadmium sulfide, zinc oxide and amorphous silicon.

Each layer of the photoreceptor can be formed by a deposition method or a method of coating a dispersion. The dispersion coating is carried out with a spin coater, an applicator, a spray coater, a dip coater, a roll coater, a curtain coater or a bead coater. The formed coating is statically dried or air-dried at a temperature between room temperature and 200° C. for 10 minutes to 6 hours. The thickness of the dry photoconductive layer is 5 to 50 µm for the photoreceptor of a single-layer type. In the photoreceptor of a dual-layer type, the thickness of the charge-generating layer is 0.01 to 5 µm, preferably 0.1 to 1 µm, and the thickness of the hole-transporting layer is 5 to 50 µm, preferably 10 to 20 µm.

The resin used for forming the photosensitive layer of the photoreceptor of a single-layer type and the charge-generating layer or hole-transporting layer of the photoreceptor of a laminate type can be selected from a wide range of insulating resins. It can be also selected from organic photoconductive polymers such as poly-N-vinylcarbozole, polyvinylanthracene and polysilanes. The above resin is preferably selected from insulating resins such as polyvinyl butyral, polyarylate, polycarbonate, polyester, phenoxy, acryl, polyamide, urethane, epoxy, silicone, polystyrene, polyvinyl chloride, a vinyl chloride-vinyl acetate copolymer, phenol and a melamine resin. The amount of the resin used for forming the charge-generating layer or the hole-transport layer is preferably 100% by weight or less of the amount of the charge-generating material or the hole-transport material. The above resins may be used in combination. No resin may be used. Further, the charge-generating layer may be formed by a physical film forming method such as a deposition or sputtering method. The deposition or sputtering is preferably carried out under vacuum atmosphere at $10^{-5}$ Torr or less. Further, the above layer may be formed in an inert gas such as nitrogen, argon or helium gas.

The solvent used for forming each layer of the electrophotographic photoreceptor is preferably selected from those solvents which do not affect the undercoat layer and other photoconductive layer. Specific examples of the solvent include aromatic hydrocarbons such as benzene and xylene, ketones such as acetone, methyl ethyl ketone and cylcohexanone, alcohols such as methanol and ethanol, esters such as ethyl acetate and methyl cellosolve, halogenated aliphatic hydrocarbons such as carbon tetrachloride, chloroform, dichloromethane, dichloroethane and trichloroethylene, halogenated aromatic hydrocarbons such as chlorobenzene and dichlorobenzene, and ethers such as tetrahydrofuran and dioxane, while the above solvent shall not be limited to these.

The hole-transporting layer is formed by applying the hole-transporting material or a solution of the hole-transporting material in an insulating resin. The hole-transporting material used for the photoreceptor of the present invention may be a combination of the compound of the formula (1) with other hole-transporting material. The compound of the formula (1) is that which is converted to a polymer having a high molecular weight, and it is therefore not necessary to use other insulating resin. When the compound of the formula (1) is used in combination with an insulating resin for improving the photoreceptor in heat resistance and wear resistance, the compound of the formula (1) is advantageous for improving the sensitivity and durability, since it has excellent compatibility with a resin so that a crystal of a formed thin film is hardly deposited.

For improving the electrophotographic properties and image properties, an undercoat layer may be provided between the substrate and the organic layer as required. The undercoat layer may be formed from any one of resins such as polyamides, casein, polyvinyl alcohol, gelatin and polyvinyl butyral and metal oxides such as aluminum oxide.

The hole-transporting material of the present invention can be suitably used not only as a hole-transport material for an organic EL device or an electrophotographic photoreceptor, but also as an organic photoconductive material for a photoelectric converter, a solar cell and an image sensor.

The present invention will be explained more in detail hereinafter with reference to Examples, in which "part" stands for "part by weight".

Synthesis of Compound (1)

10 Parts of cyclohexanone, 17 parts of triphenylamine and 0.5 parts of methanesulfonic acid were added to 15 parts of acetic acid, and the mixture was stirred under heat at 100° C. for 10 hours. Then, the reaction mixture was diluted with 500 parts of water and neutralized with a diluted sodium hydroxide aqueous solution. Then, the reaction mixture was extracted with ethyl acetate, and the extract was concentrated and purified by silica gel column chromatography to give 8 parts of a powder having white fluorescence. The powder was analyzed by GPC (gel permeation chromatography) for a molecular weight to show that the powder was Compound (1). The average molecular weight of the powder was determined by GPC as a weight average molecular weight as a polystyrene.

The results of elemental analysis of the powder were as follows.

Results of elemental analysis As $C_{66}H_{66}N_3$ Calculated (%): C: 88.58, H: 6.76, N: 4.66 Found (%): C: 88.29, H: 6.63, N: 5.08

FIG. 1 shows the infrared absorption spectrum of the above Compound (1) (KBr tablet method).

Synthesis of Compound (2)

10 Parts of cyclohexanone, 28 parts of 4-methyltriphenylamine and 1 part of methanesulfonic acid were added to 30 parts of acetic acid, and the mixture was stirred under heat at 150° C. for 30 hours. Then, the reaction mixture was diluted with 500 parts of water and neutralized with a diluted sodium hydroxide aqueous solution. Then, the reaction mixture was extracted with ethyl acetate, and the extract was concentrated and purified by silica gel column chromatography to give 13 parts of a powder having yellow fluorescence. The powder was analyzed by GPC for a molecular weight to show that the powder was Compound (2).

The results of elemental analysis of the powder were as follows.

Results of elemental analysis As $C_{144}H_{142}N_6$ Calculated (%): C: 88.43, H: 7.27, N: 4.30 Found (%): C: 88.58, H: 7.18, N: 4.24

Figure 2:
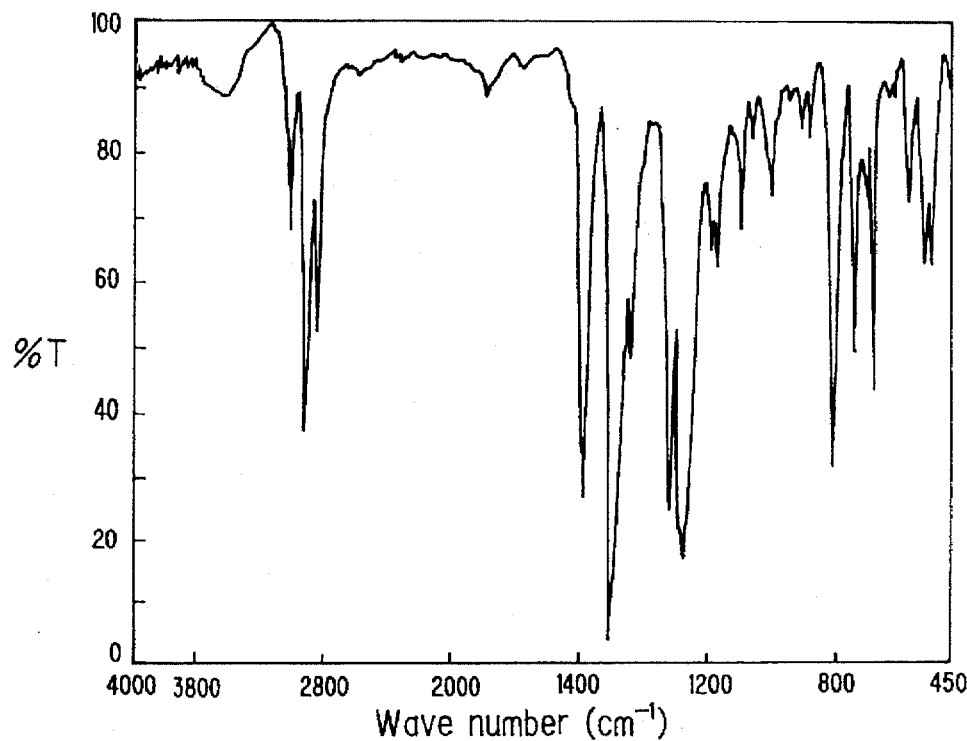
FIG. 2 shows the infrared absorption spectrum of Compound 2.

FIG. 2 shows the infrared absorption spectrum of the above Compound (2) (KBr tablet method).

Synthesis of Compound (13)

8 Parts of cyclohexanone, 25 parts of 4-methoxytriphenylamine and 1 part of methanesulfonic acid were added to 30 parts of acetic acid, and the mixture was stirred under heat at 150° C. for 30 hours. Then, the reaction mixture was diluted with 500 parts of water and neutralized with a diluted sodium hydroxide aqueous solution. Then, the reaction mixture was extracted with ethyl acetate, and the extract was concentrated and purified by silica gel column chromatography to give 13 parts of a powder having yellow fluorescence. The powder was analyzed by GPC for a molecular weight to show that the powder was Compound (13).

The results of elemental analysis of the powder were as follows.

Results of elemental analysis As $C_{225}H_{234}N_9$ Calculated (%): C: 84.27, H: 7.30, N: 3.93 Found (%): C: 84.61, H: 7.21, N: 3.85

Figure 3:
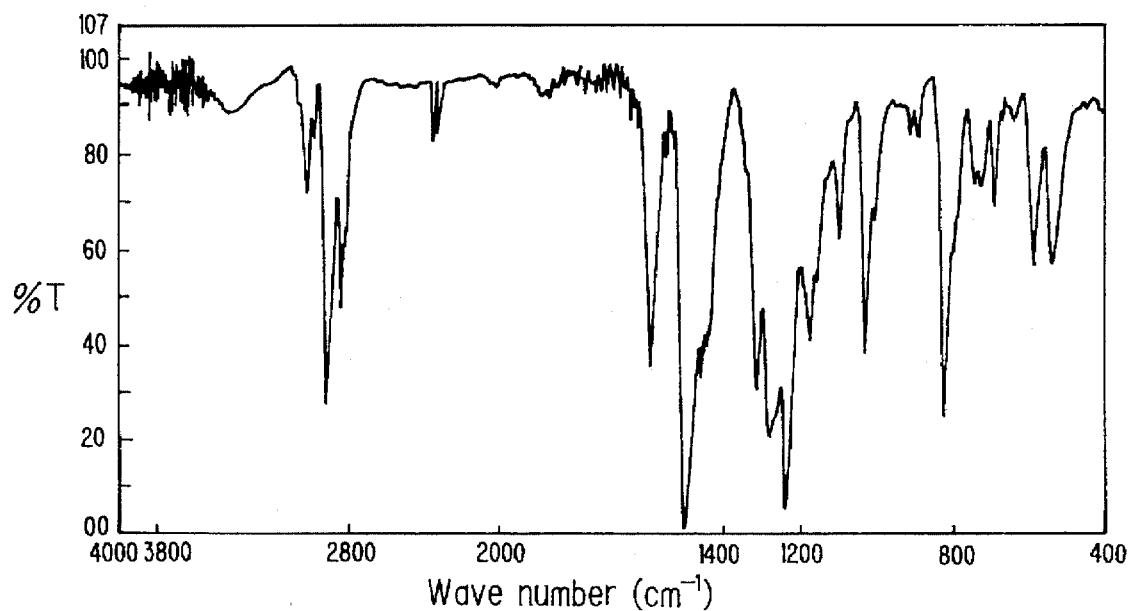
FIG. 3 shows the infrared absorption spectrum of Compound 13.

FIG. 3 shows the infrared absorption spectrum of the above Compound (13) (KBr tablet method).

Synthesis of Compound (21)

15 Parts of cyclohexanone, 24 parts of 4,4-bis(2,4-dimethylphenylphenylamino)biphenyl and 0.5 part of methanesulfonic acid were added to 25 parts of acetic acid, and the mixture was stirred under heat at 100° C. for 20 hours. Then, the reaction mixture was diluted with 500 parts of water and neutralized with a diluted sodium hydroxide aqueous solution. Then, the reaction mixture was extracted with ethyl acetate, and the extract was concentrated and purified by silica gel column chromatography to give 18 parts of a powder having white fluorescence. The powder was analyzed by GPC for a molecular weight as a styrene to show that the powder was Compound (21).

Figure 4:
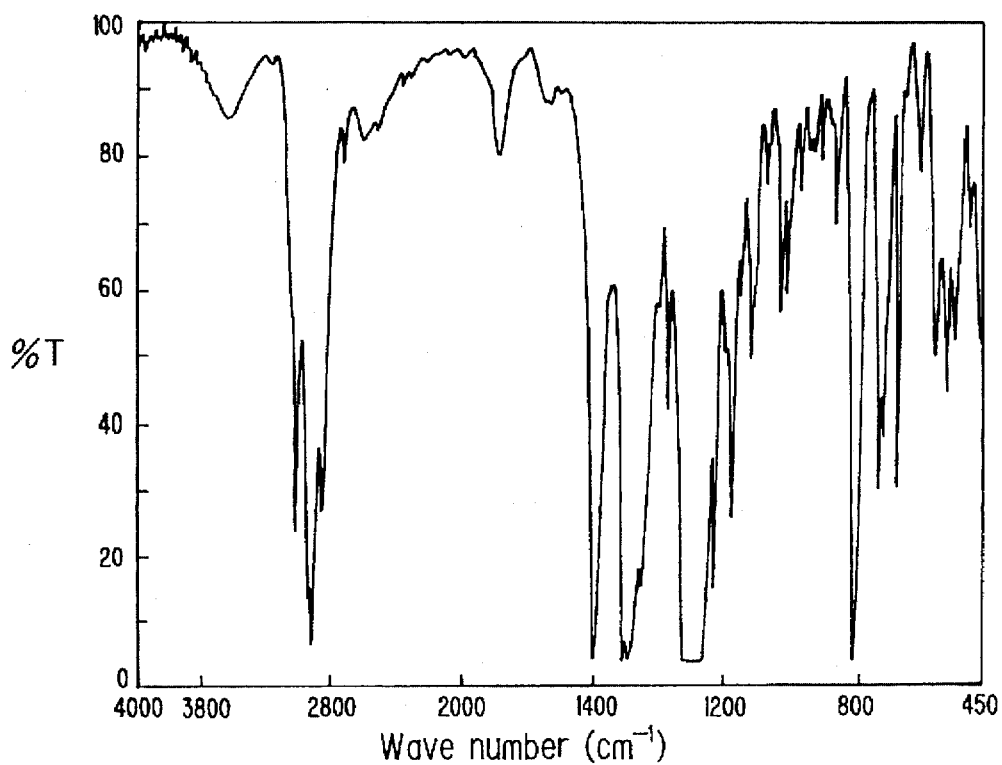
FIG. 4 shows the infrared absorption spectrum of Compound 21.

FIG. 4 shows the infrared absorption spectrum of the above Compound (21) (KBr tablet method).

Synthesis of compound (24)

18 Parts of 4-methylcyclohexanone, 20 parts of 9,10-bis (4-n-butylphenylphenylamino)phenanthrene and 0.5 part of methanesulfonic acid were added to 21 parts of acetic acid, and the mixture was stirred under heat at 100° C. for 25 hours. Then, the reaction mixture was diluted with 400 parts of water and neutralized with a diluted sodium hydroxide aqueous solution. Then, the reaction mixture was extracted with ethyl acetate, and the extract was concentrated and purified by silica gel column chromatography to give 15 parts of a powder having white fluorescence. The powder was analyzed by GPC for a molecular weight as a styrene to show that the powder was Compound (24).

Synthesis of Compound (30)

15 Parts of 4-methylcyclohexanone, 18 parts of 1,5-bis (3,4-dimethylphenylphenylamino)naphthalene and 0.5 part of methanesulfonic acid were added to 30 parts of acetic acid, and the mixture was stirred under heat at 100° C. for 80 hours. Then, the reaction mixture was diluted with 500 parts of water and neutralized with a diluted sodium hydroxide aqueous solution. Then, the reaction mixture was extracted with ethyl acetate, and the extract was concentrated and purified by silica gel column chromatography to give 7 parts of a powder having white fluorescence. The powder was analyzed by GPC for a molecular weight as a styrene to show that the powder was Compound (30).

FIG. 4 shows the infrared absorption spectrum of the above Compound (30) (KBr tablet method).

EXAMPLE 1

Compound (1), tris(8-hydroxyquinoline)aluminum complex and a polycarbonate resin (PC-A) in a weight ratio of 3:2:5 were dissolved in tetrahydrofuran, and the resultant solution was spin-coated on a cleaned glass plate with an ITO electrode to form a light-emitting layer having a thickness of 100 nm. An electrode having a thickness of 150 nm was formed thereon from an alloy of magnesium and silver in a magnesium/silver mixing ratio of 10/1, to obtain an organic EL device as shown in FIG. 5. This organic EL device showed a light emission of 180 cd/m² at a direct current voltage of 5 V.

EXAMPLE 2

Compound (2) was dissolved in tetrahydrofuran, and the resultant solution was spin-coated on a cleaned glass plate with an ITO electrode to form a hole-injecting layer having a thickness of 50 nm. Then, tris(8-hydroxyquinoline) aluminum complex was vacuum-deposited at $10^{-6}$ Torr at a substrate temperature of room temperature, to form a light-emitting layer having a thickness of 30 nm, and an electrode having a thickness of 100 nm was formed thereon from an alloy of magnesium and silver in a magnesium/silver mixing ratio of 10/1, to obtain an organic EL device as shown in FIG. 6. This organic EL device showed a light emission of about 230 cd/m² at a direct current voltage of 5 V.

EXAMPLE 3

Compound (3) was dissolved in tetrahydrofuran, and the resultant solution was spin-coated on a cleaned glass plate with an ITO electrode to form a hole-injecting layer having a thickness of 50 nm. Then, tris(8-hydroxyquinoline) aluminum complex was vacuum-deposited at $10^{-6}$ Torr at a substrate temperature of room temperature, to form a light-emitting layer having a thickness of 30 nm, and an electrode having a thickness of 100 nm was formed thereon from an alloy of magnesium and silver in a magnesium/silver mixing ratio of 10/1, to obtain an organic EL device as shown in FIG. 6. This organic EL device showed a light emission of about 400 cd/m² at a direct current voltage of 5 V.

EXAMPLE 4

An organic EL device was obtained in the same manner as in Example 3 except that Compound (3) was replaced with Compound (13). This organic EL device showed a light emission of about 510 cd/m² at a direct current voltage of 5 V.

EXAMPLE 5

An organic EL device was obtained in the same manner as in Example 3 except that Compound (3) was replaced with Compound (17). This organic EL device showed a light emission of about 420 cd/m² at a direct current voltage of 5 V.

EXAMPLE 6

An organic EL device was obtained in the same manner as in Example 3 except that Compound (3) was replaced with Compound (19). This organic EL device showed a light emission of admission of about 510 cd/m² at a direct current voltage of 5 V.

EXAMPLE 7

Compound (5) was vaccum-deposited on a cleaned glass plate with an ITO electrode to form a hole-injecting layer having a thickness of 20 nm. Further, N,N'-diphenyl-N,N'-(3-methylphenyl)-1,1'-biphenyl-4,4'-diamine was vacuum-deposited to form a hole-transporting layer having a thickness of 30 nm. Then, tris(8-hydroxyquinoline)aluminum complex was vacuum-deposited to form a light-emitting layer having a thickness of 30 nm, and an electrode having a thickness of 100 nm was formed thereon from an alloy of magnesium and silver in a magnesium/silver mixing ratio of 10/1, to obtain an organic EL device. The above hole-injecting layer and the above light-emitting layer were formed under vacuum at $10^{-6}$ Torr at a substrate temperature of room temperature. This organic EL device showed a light emission of about 310 cd/m$^2$ at a direct current voltage of 5 V.

EXAMPLE 8

N,N'-diphenyl-N,N'-(3-methylphenyl)-1,1'-biphenyl-4,4'-diamine was vacuum-deposited on a cleaned glass plate with an ITO electrode to form a hole-injecting layer having a thickness of 50 nm. Then, tris(8-hydroxyquinoline) aluminum complex and Compound (7) in an aluminum complex/Compound (7) amount ratio of 3/1 were vacuum-deposited to form a light-emitting layer having a thickness of 50 nm, and an electrode having a thickness of 150 nm was formed thereon from an alloy of magnesium and silver in a magnesium/silver mixing ratio of 10/1, to obtain an organic EL device as shown in FIG. 6. The above hole-injecting layer and the above light-emitting layer were formed under vacuum at $10^{-6}$ Torr at a substrate temperature of room temperature. This organic EL device showed a light emission of about 360 cd/m$^2$ at a direct current voltage of 5 V.

EXAMPLE 9

Compound (9) was dissolved in chloroform, and the resultant solution was spin-coated on a cleaned glass plate with an ITO electrode to form a hole-injecting layer having a thickness of 50 nm. Then, tris(8-hydroxyquinoline) aluminum complex was vacuum-deposited to form a light-emitting layer having a thickness of 50 nm, and further, [2-(4-tert-butylphenyl)-5-(biphenyl)-1,3,4-oxadiazole] was vacuum-deposited to form an electron-injecting layer having a thickness of 20 nm. An electrode having a thickness of 150 nm was formed thereon from an alloy of magnesium and silver in a magnesium/silver mixing ratio of 10/1, to obtain an organic EL device as shown in FIG. 7. This organic EL device showed a light emission of about 490 cd/m$^2$ at a direct current voltage of 5 V.

EXAMPLE 10

Tris(8-hydroxyquinoline)aluminum complex, Compound (21) and a polycarbonate resin ("Panlite L-1250", supplied by Teijin Kasei) in an amount ratio of 3/2/5 were dissolved in chloroform, and the resultant solution was spin-coated on a cleaned glass plate with an ITO electrode to form a light-emitting layer having a thickness of 100 nm. An electrode having a thickness of 150 nm was formed thereon from an alloy of magnesium and silver in a magnesium/silver mixing ratio of 10/1, to obtain an organic EL device as shown in FIG. 5. This organic EL device showed a light emission of about 160 cd/m$^2$ at a direct current voltage of 5 V and a light emission efficiency of 1.51 lm/W.

EXAMPLE 11

Compound (22) was vaccum-deposited on a cleaned glass plate with an ITO electrode to form a hole-injecting layer having a thickness of 30 nm. Then, tris(8-hydroxyquinoline) aluminum complex was vacuum-deposited to form a light-emitting layer having a thickness of 50 nm, and an electrode having a thickness of 1,500 angstroms was formed thereon from an alloy of magnesium and silver in a magnesium/silver mixing ratio of 10/1, to obtain an organic EL device as shown in FIG. 6. The above hole-injecting layer and the above light-emitting layer were formed under vacuum at $10^{-6}$ Torr at a substrate temperature of room temperature. This organic EL device showed a light emission of about 440 cd/m$^2$ at a direct current voltage of 5 V and a light emission efficiency of 2.41 lm/W.

EXAMPLE 12

Compound (23) was vaccum-deposited on a cleaned glass plate with an ITO electrode to form a hole-injecting layer having a thickness of 30 nm. Then, tris(8-hydroxyquinoline) aluminum complex was vacuum-deposited to form a light-emitting layer having a thickness of 20 nm, and further, [2-(4-tert-butylphenyl)-5-(biphenyl)-1,3,4-oxadiazole] was vacuum-deposited to form an electron-injecting layer having a thickness of 20 nm. An electrode having a thickness of 150 nm was formed thereon from an alloy of magnesium and silver in a magnesium/silver mixing ratio of 10/1, to obtain an organic EL device as shown in FIG. 7. This organic EL device showed a light emission of about 360 cd/m$^2$ at a direct current voltage of 5 V and a light emission efficiency of 2.21 lm/W.

EXAMPLES 13–39

Compound (one of Compounds (24) to (50)) shown in Table 3 was dissolved in chloroform, and the resultant solution was spin-coated on a cleaned glass plate with an ITO electrode to form a hole-injecting layer having a thickness of 50 nm. Then, tris(8-hydroxyquinoline)aluminum complex was vacuum-deposited to form a light-emitting layer having a thickness of 30 nm, and an electrode having a thickness of 100 nm was formed thereon from an alloy of magnesium and silver in a magnesium/silver mixing ratio of 10/1, to obtain an organic EL device as shown in FIG. 6. The above light-emitting layer was formed under vacuum at $10^{-6}$ Torr at a substrate temperature of room temperature. The so-obtained organic EL device showed a light emission as shown in Table 4 a direct current voltage of 5 V.

TABLE 4

| Example | Compound | Light emission brightness (cd/m$^2$) | Light emission efficiency (lm/W) |
|---|---|---|---|
| 13 | (24) | 510 | 4.0 |
| 14 | (25) | 450 | 3.5 |
| 15 | (26) | 490 | 4.1 |
| 16 | (27) | 520 | 4.2 |
| 17 | (28) | 510 | 4.0 |
| 18 | (29) | 510 | 4.0 |
| 19 | (30) | 500 | 3.8 |
| 20 | (31) | 480 | 3.7 |
| 21 | (32) | 470 | 3.6 |
| 22 | (33) | 510 | 3.9 |
| 23 | (34) | 500 | 3.9 |
| 24 | (35) | 530 | 4.2 |
| 25 | (36) | 490 | 4.1 |
| 26 | (37) | 460 | 3.9 |
| 27 | (38) | 500 | 3.8 |
| 28 | (39) | 490 | 3.9 |
| 29 | (40) | 510 | 4.0 |
| 30 | (41) | 460 | 3.8 |
| 31 | (42) | 450 | 3.8 |
| 32 | (43) | 500 | 4.0 |
| 33 | (44) | 490 | 3.8 |
| 34 | (45) | 550 | 4.1 |
| 35 | (46) | 480 | 3.9 |
| 36 | (47) | 510 | 3.9 |
| 37 | (48) | 500 | 3.8 |
| 38 | (49) | 490 | 3.7 |
| 39 | (50) | 520 | 4.0 |

Comparative Example 1

An organic EL device was obtained in the same manner as in Example 2 except that the raw material for a hole-injecting layer was replaced with N,N'-(4-methylphenyl)-N, N'-(4-n-butylphenyl)-phenanthrene-9,10-diamine. This organic EL device showed a light emission of about 390 cd/m$^2$ at a direct current voltage of 5 V and a light emission efficiency of 2.01 lm/W.

When all the organic EL devices obtained in Examples 1 to 39 were allowed to emit light at 1 mA/cm$^2$, they stably emitted light for more than 1,000 hours.

The organic EL device of the present invention accomplishes improvement in light emission efficiency and brightness and a long working life as a device, and no limitation shall be imposed on the light-emitting material, light-emitting auxiliary material, hole-transporting material, electron-transporting material, sensitizer, resin and electrode material used in combination and the method for the production thereof.

EXAMPLE 40

4 Grams of ε-form phthalocyanine, 2 g of Compound (2) and 14 g of a polyester resin (Vylon 200, supplied by Toyobo Co., Ltd.) were dispersed with a ball mill together with 80 g of tetrehydrofuran for 5 hours. The resultant dispersion was applied to an aluminum substrate and dried to give a single-layer type electrophotographic photoreceptor having a thickness of 20 μm, as shown in FIG. 8.

EXAMPLE 41

6 Grams of dibromoanthanthrone 2 g of Compound (6) and 12 g of a polyester resin (Vylon 200, supplied by Toyobo Co., Ltd.) were dispersed with a ball mill together with 80 g of tetrehydrofuran for 5 hours. The resultant dispersion was applied to an aluminum substrate and dried to give a single-layer type electrophotographic photoreceptor having a thickness of 20 μm, as shown in FIG. 8.

EXAMPLE 42

2 Grams of τ-form phthalocyanine and 2 g of a polyvinyl butyral resin ("BH-3", supplied by Sekisui Chemical Co., Ltd.) were dispersed with a ball mill together with 96 g of tetrehydrofuran for 2 hours. The resultant dispersion was applied to an aluminum substrate and dried to give a charge-generating layer having a thickness of 0.3 μm. Then, 10 g of Compound (10) and 10 g of a polycarbonate resin ("L-1250", supplied by Teijin Kasei) were dissolved in 80 g of dichloromethane, and the resultant solution was applied to the charge-generating layer and dried to give a hole-transporting layer having a thickness of 20 μm, whereby an electrophotographic photoconductive plate of a dual-layer type as shown in FIG. 9 was obtained.

EXAMPLE 43

An electrophotographic photoconductive plate of a dual-layer type was obtained in the same manner as in Example 42 except that Compound (10) was replaced with Compound (16).

EXAMPLE 44

An electrophotographic photoconductive plate of a dual-layer type was obtained in the same manner as in Example 42 except that Compound (10) was replaced with Compound (18).

EXAMPLE 45

2 Grams of N,N'-bis(2,6-dichlorophenyl)-3,4,9,10-perylenedicarboxyimide and 2 g of a polyvinyl butyral resin ("BH-3", supplied by Sekisui Chemical Co., Ltd.) were dispersed with a ball mill together with 96 g of tetrehydrofuran for 2 hours. The resultant dispersion was applied to an aluminum substrate and dried to give a charge-generating layer having a thickness of 0.3 μm. Then, 10 g of Compound (12) and 10 g of a polycarbonate resin ("L-1250", supplied by Teijin Kasei) were dissolved in 80 g of dichloromethane, and the resultant solution was applied to the charge-generating layer and dried to give a hole-transporting layer having a thickness of 20 μm, whereby an electrophotographic photoconductive plate of a dual-layer type as shown in FIG. 9 was obtained.

EXAMPLE 46

4 Grams of ε-form phthalocyanine, 2 g of Compound (28) and 14 g of a polyester resin (Vylon 200, supplied by Toyobo Co., Ltd.) were dispersed with a ball mill together with 80 g of tetrehydrofuran for 5 hours. The resultant dispersion was applied to an aluminum substrate and dried to give a single-layer type electrophotographic photoreceptor having a thickness of 20 μm, as shown in FIG. 8.

EXAMPLE 47

6 Grams of dibromoanthanthrone 2 g of Compound (30) and 12 g of a polyester resin (Vylon 200, supplied by Toyobo Co., Ltd.) were dispersed with a ball mill together with 80 g of tetrehydrofuran for 5 hours. The resultant dispersion was applied to an aluminum substrate and dried to give a single-layer type electrophotographic photoreceptor having a thickness of 20 μm, as shown in FIG. 8.

EXAMPLE 48

2 Grams of N,N'-bis(2,6-dichlorophenyl)-3,4,9,10-perylenedicarboxyimide and 2 g of a polyvinyl butyral resin ("BH-3", supplied by Sekisui Chemical Co., Ltd.) were dispersed with a ball mill together with 96 g of tetrehydrofuran for 2 hours. The resultant dispersion was applied to an aluminum substrate and dried to give a charge-generating layer having a thickness of 0.3 μm. Then, 10 g of Compound (35) and 10 g of a polycarbonate resin ("L-1250", supplied by Teijin Kasei) were dissolved in 80 g of dichloromethane, and the resultant solution was applied to the charge-generating layer and dried to give a hole-transporting layer having a thickness of 20 μm, whereby an electrophotographic photoconductive plate of a dual-layer type as shown in FIG. 9 was obtained.

EXAMPLES 49-78

2 Grams of τ-form phthalocyanine and 2 g of a polyvinyl butyral resin ("BH-3", supplied by Sekisui Chemical Co., Ltd.) were dispersed with a ball mill together with 96 g of tetrehydrofuran for 2 hours. The resultant dispersion was applied to an aluminum substrate and dried to give a charge-generating layer having a thickness of 0.3 μm. Then, 10 g of Compound shown in Table 4 and 10 g of a polycarbonate resin ("L-1250", supplied by Teijin Kasei) were dissolved in 80 g of dichloromethane, and the resultant solution was applied to the charge-generating layer and dried to give a hole-transporting layer having a thickness of 20 μm. In the above manner, electrophotographic photoconductive plates of a dual-layer type as shown in FIG. 9 were obtained.

Each electrophotographic photoconductive plate was set in an electrostatic paper analyzer (EPA-8100, supplied by Kawaguchi Denki Seisakusho), and exposed to white light (5 lux) at a static mode of 2 at a corona charge of −5.2 KV to determine a ratio (dark decay ratio: $DDR_2=V_2/V_0$) between an initial surface potential ($V_0$) and a surface potential ($V_2$) after the photoconductive plate was allowed to stand in a dark place for 2 seconds, a half exposure sensitivity ($E_{1/2}$) on the basis of a time during which the charge amount decreased to ½ of the initial charge amount, and a surface potential ($VR_3$) after 3 seconds from the optical exposure. Table 5 shows the electrophotographic properties of the electrophotographic photoconductive plates obtained in Examples 40 to 78.

TABLE 5

| Example | Compound | $V_0$ (−V) | $DDR_2$ (%) | $E_{1/2}$ (lux · s) | $VR_3$ (−V) |
|---|---|---|---|---|---|
| 40 | (4) | 540 | 94 | 2.9 | 30 |
| 41 | (6) | 580 | 96 | 3.8 | 25 |
| 42 | (10) | 690 | 97 | 1.0 | 8 |
| 43 | (16) | 680 | 95 | 1.1 | 7 |
| 44 | (18) | 650 | 95 | 1.0 | 5 |
| 45 | (12) | 670 | 94 | 1.8 | 10 |
| 46 | (28) | 610 | 92 | 2.5 | 20 |
| 47 | (30) | 630 | 95 | 2.8 | 15 |
| 48 | (33) | 810 | 95 | 1.5 | 7 |
| 49 | (21) | 800 | 95 | 0.6 | 10 |
| 50 | (22) | 820 | 95 | 0.6 | 5 |
| 51 | (23) | 800 | 94 | 0.6 | 5 |
| 52 | (24) | 810 | 95 | 0.6 | 7 |
| 53 | (25) | 830 | 96 | 0.7 | 8 |
| 54 | (26) | 810 | 95 | 0.6 | 6 |
| 55 | (27) | 800 | 95 | 0.7 | 7 |
| 56 | (28) | 830 | 96 | 0.7 | 5 |
| 57 | (29) | 810 | 95 | 0.7 | 10 |
| 58 | (30) | 820 | 94 | 0.7 | 8 |
| 59 | (31) | 790 | 93 | 0.7 | 6 |
| 60 | (32) | 810 | 95 | 0.6 | 8 |
| 61 | (33) | 790 | 94 | 0.7 | 5 |
| 62 | (34) | 820 | 95 | 0.8 | 8 |
| 63 | (35) | 780 | 93 | 0.8 | 8 |
| 64 | (36) | 810 | 95 | 0.6 | 15 |
| 65 | (37) | 810 | 94 | 0.7 | 1 |
| 66 | (38) | 770 | 93 | 0.6 | 2 |
| 67 | (39) | 820 | 96 | 0.7 | 3 |
| 68 | (40) | 800 | 95 | 0.6 | 2 |
| 69 | (41) | 800 | 97 | 0.6 | 5 |
| 70 | (42) | 800 | 95 | 0.7 | 7 |
| 71 | (43) | 820 | 96 | 0.6 | 5 |
| 72 | (44) | 820 | 97 | 0.6 | 5 |
| 73 | (45) | 810 | 98 | 0.7 | 8 |
| 74 | (46) | 800 | 97 | 0.6 | 5 |
| 75 | (47) | 780 | 97 | 0.6 | 5 |
| 76 | (48) | 810 | 97 | 0.6 | 5 |
| 77 | (49) | 800 | 95 | 0.6 | 5 |
| 78 | (50) | 810 | 96 | 0.7 | 8 |

Comparative Example 2

An electrophotographic photoreceptor was obtained in Example 49 except that the hole-transporting material was replaced with N,N'-(4-methylphenyl)-N,N'-(4-n-butylphenyl)-phenanthrene-9,10-diamine. The electrophotographic properties of the electrophotographic photoreceptor were that $V_0$=−700 (V), $DDR_2$=90 (%), $E_{1/2}$=0.9 (lux.s) ad $VR_3$=−25 (V), or were inferior to those of the electrophotographic photoreceptor for which the hole-transporting material of the present invention was adapted. After the above electrophotographic photoreceptor was used in the continuous operation of more than 10,000 times, the electrophotographic photoreceptor showed a change ratio in electrophotographic properties such as surface potential and sensitivity and image density by more than 10%. This large change ratio means unstable electrophotographic properties, and no images of high quality are obtained.

After the organic EL devices obtained in Examples 1 to 39 were allowed to continuously emit light at 1 mA/cm² for 1,000 hours, all of them retained more than 50% of their initial brightness, whereas the device obtained in Comparative Example 1 showed less than 50% of its initial brightness only after 100 hours, and the number of dark spots also increased. The hole-transporting material of the present invention is that which is converted to a polymer having a high molecular weight so that it is remarkably improved in heat resistance as an organic EL device. All the compounds of the formula (1) have a glass transition temperature of at least 140° C. and a melting point of at least 280° C., while the aromatic amine derivatives as typical examples of the hole-transporting material have a glass transition temperature of 60° to 70° C. and a melting point of 160° to 180° C. These data clearly shows that the hole-transporting material of the present invention is greatly improved.

According to the present invention, compounds having excellent hole-transporting capability can be obtained. The hole-transporting compounds provided by the present invention give organic EL devices having high light emission efficiency and brightness and a long working life and electrophotographic photoreceptors which are excellent in initial electrophotographic properties such as sensitivity, hole-transporting properties, surface potential, dark attenuation ratio and photosensitivity and which show decreased fatigue when used repeatedly.

What is claimed is:

1. In an organic EL device which comprises (1) a pair of electrodes and a light-emitting layer formed of an organic compound layer placed between the pair of electrodes, or (2) a pair of electrodes and a plurality of organic compound layers including a light-emitting layer and a hole-injection layer placed between the pair of electrodes, the improvement wherein the light-emitting layer or the hole-injection layer contains a hole-transporting material of the formula (1)

$$H\text{—}A\text{—}[\text{—}B\text{—}A\text{—}]_n\text{—}B\text{—}A\text{—}H \quad (1)$$

wherein A is an aromatic amine derivative residue of the following formula (2), B is a residue of the following formula (3), and n is an integer of 1 to 5,000, Formula (2):

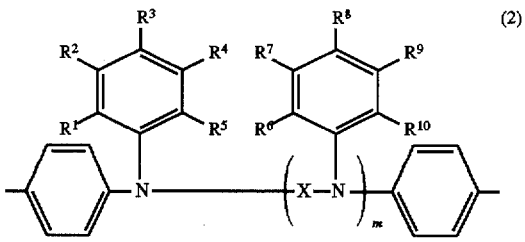

wherein each of $R^1$ to $R^{10}$ is independently hydrogen, halogen, an unsubstituted alkyl group, a substituted alkyl group, an unsubstituted alkoxy group, a substituted alkoxy group, an unsubstituted thioalkoxy group, a substituted thioalkoxy group, a cyano group, an amino group, mono- or disubstituted amino group, a hydroxyl group, a mercapto group, an unsubstituted aryloxy group, a substituted aryloxy group, an unsubstituted arylthio group, a substituted arylthio group, an unsubstituted aromatic group, a substituted aromatic group, an unsubstituted heterocyclic group or a substituted heterocyclic group, and wherein adjacent substituents among $R^1$ to $R^{10}$ may form a substituted or unsubstituted ring or rings, X is a divalent aromatic residue or —Ar—Z—Ar— in which Ar is an aromatic residue having 6 to 20 carbon atoms and Z is a direct bond, oxygen, sulfur, selenium, an aromatic residue which may contain any one of oxygen, sulfur and selenium, or a divalent aliphatic residue which may contain any one of oxygen, sulfur and selenium, and m is an integer of 0 or 1, Formula (3):

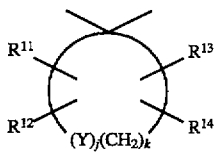

wherein each of $R^{11}$ to $R^{14}$ is independently hydrogen, halogen, an unsubstituted alkyl group, a substituted alkyl group, an unsubstituted alkoxy group, a substituted alkoxy group or a disubstituted amino group, and wherein adjacent substituents among $R^{11}$ to $R^{14}$ may form a substituted or unsubstituted ring, Y is oxygen, sulfur or monosubstituted nitrogen, j is an integer of 0 or 1 and k is an integer of 4 to 7.

2. An organic EL device according to claim 1 wherein each of $R^1$ to $R^{10}$ in the formula (2) is independently hydrogen, an unsubstituted alkyl group, an unsubstituted alkoxy group or a dialkyl-substituted amino group.

3. An organic EL device according to claim 1, wherein X in the formula (2) is a phenylene, biphenylene, substituted biphenylene, terphenylene, naphthylene or anthranylene.

4. An organic EL device according to claim 1, wherein the compound of the formula (3) is 1,1-cyclopentylene, 1,1-cyclohexylene, 1,1-cycloheptylene, 1,1-cyclooctylene or any one of these in which an alkyl group is substituted.

5. An organic EL device according to claim 1 wherein the layer containing the hole-transporting material is the light-emitting layer.

6. An organic EL device according to claim 1, wherein said device has a hole-injecting layer formed on an anode and the light-emitting layer formed on the hole-injecting layer, and said hole-injecting layer contains the hole-transporting material of formula (1).

7. An organic EL device according to claim 1, wherein said device has a hole-injecting layer formed on an anode, a hole-transporting layer formed on the hole-injecting layer and the light-emitting layer formed on the hole-transporting layer, and said hole-injecting layer contains the hole-transporting material of formula (1).

8. An organic EL device according to claim 1, wherein said device has a hole-injecting layer formed on an anode, the light-emitting layer formed on the hole-injecting layer and an electron-injecting layer formed on the light-emitting layer, and said hole-injecting layer contains the hole-transporting material of formula (1).

* * * * *